United States Patent [19]
Coupland

[11] Patent Number: 5,994,404
[45] Date of Patent: Nov. 30, 1999

[54] NERVONIC ACID COMPOSITIONS

[75] Inventor: Keith Coupland, Hotham, United Kingdom

[73] Assignee: Croda International PLC, North Humberside, United Kingdom

[21] Appl. No.: 08/793,081

[22] PCT Filed: Aug. 21, 1995

[86] PCT No.: PCT/GB95/01985

§ 371 Date: Feb. 14, 1997

§ 102(e) Date: Feb. 14, 1997

[87] PCT Pub. No.: WO96/05740

PCT Pub. Date: Feb. 29, 1996

[30] Foreign Application Priority Data

Aug. 19, 1994 [GB] United Kingdom .................. 9416846

[51] Int. Cl.$^6$ .............................. A61K 31/20; A23D 7/00
[52] U.S. Cl. .......................... 514/560; 426/601; 426/606; 426/607
[58] Field of Search ..................................... 426/607, 606, 426/601; 514/560

[56] References Cited

U.S. PATENT DOCUMENTS

| | | | |
|---|---|---|---|
| 5,043,179 | 8/1991 | Klemann et al. | 426/531 |
| 5,190,783 | 3/1993 | Klemann et al. | 426/531 |
| 5,411,756 | 5/1995 | Wheeler et al. | 426/607 |

FOREIGN PATENT DOCUMENTS

| | | |
|---|---|---|
| 0289968 | 11/1988 | European Pat. Off. . |
| 0319360 | 6/1989 | European Pat. Off. . |

OTHER PUBLICATIONS

International Publication No. WO 91/07955 to K. Coupland et al. entitled, "Use of Nervonic Acid . . . Disorders" dated Jun. 13, 1991.
International Publication No. WO 89/00895 to T. Grebinski entitled, "Surface Treatment to Remove Impurities in Microprocesses" dated Feb. 9, 1989.
J.R. Sargent et al., "Nervonic Acid and Demyelinating Disease" in *Medical Hypotheses* (1994) 42, 237–242.
Database WPI, Section Ch, Week 9329, Derwent, JP,A, 05155803 (Hohnen Oil), Jun. 22, 1993.
Database WPI, Section Ch, Week 9150, Derwent, JP,A, 03244344 (Moringa Milk), Oct. 31, 1991.
Database WPI, Section Ch, Week 8401, Derwent, JP,A, 58198245 (Fuji Oil), Nov. 18, 1983.
Database WPI, Section Ch, Week 8644, Derwent, JP,A, 61209544 (Ueda Seiyu et al.), Sep. 17, 1986.

*Primary Examiner*—Theodore J. Criares
*Attorney, Agent, or Firm*—Stevens, Davis, Miller & Mosher, L.L.P.

[57] ABSTRACT

A baby or infant composition is provided which comprises one or more nutrient materials and, as a supplement, nervonic acid or a functional derivative thereof or an immediate biochemical precursor of either nervonic acid or a functional derivative thereof, in a physiologically acceptable form. It has been found to be beneficial to administer such a composition to preterm babies and term babies and infants. It has also been to be beneficial to administer nervonic acid or a functional derivative thereof or an immediate biochemical precursor of either nervonic acid or a functional derivative thereof to adults having normal levels of nervonic acid in their body and, in particular, to women who intend to become pregnant, pregnant women and lactating women.

24 Claims, No Drawings

NERVONIC ACID COMPOSITIONS

This application is a 371 of PCT/GB95/01985 filed Aug. 21, 1995.

This invention relates to certain nervonic acid-containing compositions.

Nervonic acid is a long chain mono-unsaturated fatty acid, the systematic name of which is cis-tetracos-15-enoic acid, generally designated in short as C24:1(n-9). It plays a part in the biosynthesis of myelin and it is found in sphingolipids of white matter in the human brain. In diseases involving demyelination, such as adrenoleucodystrophy (ALD) and multiple sclerosis (MS), there is a marked reduction from normal in the nervonic acid levels in sphingolipids, and we have described the administration of nervonic acid to sufferers of these diseases to alleviate the condition. However, whilst this treatment is effective, its apparent simplicity belies the extreme complexity of the body processes involved. It is not the case that mere administration of a fatty acid will necessarily, or even probably, overcome a deficiency of that acid in the brain: the processes are too complex for such an elementary analysis.

In Medical Hypotheses (1994), 42, 237–242, Sargent J. R. et al review the relation between nervonic acid and demyelinating diseases. These diseases tend to occur from teenage onwards whereas, in contrast, myelin formation occurs before birth and in the first year or two of life. Sargent et al hypothesise that in the context of ALD and MS diseases, the absence of relatively specialised fatty acids during the early years of life could have serious consequences for neural performance later. Whilst, later in life, there is an apparent relationship during demyelination between nervonic acid levels and the diseases ALD and MS, no such relationship has been established between any particular acid and the myelination process itself. Indeed, the whole area of long chain fatty acid biosynthesis is proving much more complex than hitherto realised, and the effects of competing processes and variations in dietary feed are very far from understood.

We have now found, however, that despite the fundamental lack of understanding of the technology and the complexity and inter-relation of very many different factors, there is an advantage in providing a supplement of nervonic acid in the diets of children and mothers, and in the diets of adults whose nervonic acid levels are generally taken to be normal. This dietary supplement of nervonic acid other than for the treatment of a demyelinating disease provides advantageous effects both for children in the myelinating age and later in life. This finding is contrary to the generally accepted view that normal diets do result in adequate nervonic acid levels, and it is of note that despite the complexity of the overall situation, dietary nervonic acid is a useful way of providing this substance to human tissue.

According to the present invention, therefore, there is provided a baby or infant food composition comprising one or more nutrient materials and, as a supplement, nervonic acid or a functional derivative thereof or an immediate biochemical precursor of either nervonic acid or a functional derivative thereof, in a physiologically acceptable form.

The composition may, for example, comprise a formula for preterm babies or term babies and infants in the form of a ready-to-feed liquid water-based preparation, or may be in the form of a powder or concentrated liquid intended to be diluted with water to become a ready-to-feed liquid. Alternatively, infant foods, such as processed meats, vegetables and fish, can be supplemented by adding nervonic acid or a functional derivative thereof or an immediate biochemical precursor.

The term "functional derivative", as used throughout the specification, is defined as any derivative of nervonic acid which contains the intact acyl group. Examples of such functional derivatives include esters, particularly glyceride esters, for example the mono-, di- and tri-nervonyl glycerides, and ethyl esters, and fatty acid salts, such as sodium salts, lithium salts, potassium salts, calcium salts, amino acid salts and the like.

The functional derivative may be a complex triglyceride, by which is meant a triglyceride which contains, in addition to an acyl group of nervonic acid, acyl groups of other fatty acids. For example, the other acyl groups may be derived from (n-3) polyunsaturated fatty acids and (n-6) polyunsaturated acids, where (n-3) and (n-6) indicate the position of the first carbon-carbon double bond with respect to the terminal methyl group on the fatty acid. Examples of such fatty acids are 18:3(n-3) linolenic acid, 18:4(n-3) stearidonic acid, 20:5(n-3) eicosapentaenoic acid (EPA), 22:6(n-3) docosahexaenoic acid (DHA), 18:2(n-6) linoleic acid, 18:3(n-6)γ-linolenic acid, 20:3(n-6) dihomo-γ-linolenic acid and 20:4 (n-6) arachidonic acid.

Preferably, the nervonic acid is used in the form of an ester thereof, and most preferably in the form of a glyceride ester.

An immediate biochemical precursor of either nervonic acid or a functional derivative thereof can be used in the composition, as the precursor can be converted to nervonic acid or a functional derivative thereof in the body. For example, the composition may contain erucic acid.

Among the nutrients suitably present in the baby or infant composition are, for example, fats, carbohydrates, proteins, amino acids, mineral salts, nucleosides, nucleotides and vitamins.

The composition may also contain additives such as flavouring agents, colourants, thickeners, emulsifiers and other such agents, which are conventional in the art.

Preferably, the nervonic acid or functional derivative thereof comprises at least 0.5 wt % of the baby or infant composition.

According to another aspect of the present invention, there is provided the use of nervonic acid or a functional derivative thereof or an immediate biochemical precursor of either nervonic acid or a functional derivative thereof as a supplement for a baby or infant food.

We have also found that it is particularly beneficial to supplement infant formulae feeds with nervonic acid when the feed contains DHA and arachidonic acid. We believe that the presence of DHA and arachidonic acid inhibits the conversion of oleic acid to nervonic acid, thus making it even more important to supplement the feed with nervonic acid.

In humans, the essential fatty acid, linolenic acid is converted to DHA and another essential fatty acid, linoleic acid is converted to arachidonic acid. The same enzyme systems bring about these two conversions. Thus, the presence of an excess of linoleic acid will inhibit the conversion of linoleic acid to DHA, so that arachidonic acid but not DHA is produced; and equally, the presence of an excess of linolenic acid will inhibit the conversion of linoleic acid to arachidonic acid, so that DHA but not arachidronic acid is produced. Moreover, the presence of the end product DHA will inhibit the conversion of linolenic acid to DHA and probably also the conversion of linoleic acid to arachidonic acid; and equally, the presence of the end product arachidonic acid will inhibit the conversion of linoleic acid to arachidonic acid.

We have now discovered that the competitive interactions between linolenic and linoleic acid referred to above also extend to the conversion of oleic acid to nervonic acid, i.e. linolenic and linoleic acid will compete with oleic acid for conversion to long chain (C20 and C22) products. Equally, we believe that the end product inhibitions exerted by DHA and arachidonic acid on the conversions of linolenic acid to DHA and linoleic acid to arachidonic acid apply also to the conversion of oleic acid to nervonic acid.

We have now realised, therefore, that when infant formulae feeds contain the end products DHA and arachidonic acid (which is sometimes the case), it is particularly important to supplement the feed with nervonic acid or a functional derivative thereof.

According to a further aspect of the present invention, there is provided the use of nervonic acid or a functional derivative thereof or an immediate biochemical precursor of either nervonic acid or a functional derivative thereof, and one or more nutrient materials as a baby or infant food composition.

The invention also provides the use of nervonic acid or a functional derivative thereof or an immediate biochemical precursor of either nervonic acid or a functional derivative thereof as a supplement for an adult foodstuff for an adult having a normal level of nervonic acid in the body. Most preferably, the adult foodstuff is for administration to women who intend to become pregnant, pregnant women and lactating women.

In Medical Hypotheses (1994), 42, pages 237–242, Sargent J. R. et al, referred to above, figures are given for what are considered to be normal levels of nervonic acid.

The table given below illustrates the amount of nervonic acid in sphingolipids of white matter from post mortem brains of "normal individuals" and multiple sclerosis patients.

| Fatty acid | Sphingomyelin | | Sulphatides | | Cerebrosides | |
| --- | --- | --- | --- | --- | --- | --- |
| | Normal | MS | Normal | MS | Normal | MS |
| Nervonic Acid | 36.3 ± 2.5 | 25.7 ± 5.7 | 36.2 ± 3.7 | 28.0 ± 4.8 | 40.3 ± 5.7 | 31.0 ± 5.3 |

Total lipid was extracted by chloroform:methanol (2:1 vol:vol), separated by two dimensional thin layer chromatography, and fatty acid methyl esters prepared by acid-catalysed transmethylation and analysed by high resolution gas-liquid chromatography. Values are means ±s.d. for separate determinations of post mortem brain samples from 9 normal individuals and 9 patients with multiple sclerosis.

The present invention also provides the use of nervonic acid or a functional derivative thereof or an immediate biochemical precursor of either nervonic acid or a functional derivative thereof, and one or more nutrient materials as an adult foodstuff for an adult having a normal level of nervonic acid in the body, most preferably, the adult foodstuff is for administration to women who intend to become pregnant, pregnant women and lactating women.

In accordance with the present invention, there is provided the use of nervonic acid or a functional derivative thereof or an immediate biochemical precursor of either nervonic acid or a functional derivative thereof, in a physiologically acceptable form, in the manufacture of a medicament to treat preterm babies and term babies and infants, women who intend to become pregnant, pregnant women and lactating women.

The present invention also provides a foodstuff for a women who intends to become pregnant, a pregnant woman or a lactating woman, which woman has a normal level of nervonic acid in the body, to which foodstuff is added nervonic acid or a functional derivative thereof or an immediate biochemical precursor of either nervonic acid or a functional derivative thereof.

Any known foodstuff or dietary composition can be mixed with the nervonic acid or functional derivative thereof or immediate biochemical precursor, to provide a baby or infant food composition in accordance with the present invention, or an adult foodstuff for administration to adults whose nervonic acid levels are normal.

Without limitation, foodstuffs or dietary compositions which can be used to prepare the baby or infant compositions or adult foodstuffs include: oils, low fat spreads, margarines, butter, cheese spreads, milk, yoghurts, chocolate, chocolate spreads, peanut butter, salad dressing, mayonnaise, meat paste, fish paste, vegetable spreads, juices, drinks, milk, infant food, infant milk, whips, creams, powders, granules and tablets or pills containing them, capsules, bakery products, pâtés and seafood products.

Functional derivatives of nervonic acid, in a physiologically acceptable form, containing between 1 and 99% nervonic acid can be used by food manufacturers.

For example, oils containing nervonic acid or a functional derivative thereof can be used for direct ingestion or for mixing with other oily foods, such as salad oils or cooking oils. The nervonic acid or functional derivatives thereof may be mixed at between 0.5%–50%.

Compounded foodstuffs, such as whips, creams, emulsions or mayonnaise, can be supplemented by adding 0.5%–50% of nervonic acid or a functional derivative thereof.

Animal milk from cows and goats can be supplemented by adding nervonic acid or a functional derivative thereof in the range 0.5–10%, usually with addition of an emulsifier to aid incorporation.

Granules, powders and foodstuffs containing granules or powders can be prepared by adsorption or microencapsulating nervonic acid or a functional derivative thereof. Concentration levels of between 0.5 and 90% of nervonic acid or a functional derivative are envisaged.

Tablets or pills can be prepared from granules or powders containing nervonic acid or a functional derivative thereof.

Infant foods, such as processed meats, vegetables and fish, can be supplemented by adding between 0.5–50% of nervonic acid or a functional derivative thereof.

Enteral foods or infant foods can be prepared containing between 0.5–20% nervonic acid or a functional derivative thereof.

Suitably, the baby or infant food compositions of the invention, or supplements therefor, and adult foodstuffs or supplements for adult foodstuffs, for administration to adults whose nervonic acid levels are normal in accordance with the invention, comprise the oil from a plant or microorganism in a substantially purified form. Although nervonic acid is rare or insignificant in normal diets, it does occur in a small number of plant seeds and micro-organisms. Natural sources include the seed oils of *Cardamine gracea, Heliphila longifola, Thlaspi perfoliatum, Tropaeolum speciosum, Lunaria biennis, Lunaria annua* and *Malania oleifera;* the moulds *Neocallismastix frontalis, Erysiphe graminis* and *Sphaerotheca humuli;* the bacterium *Pseudomonas atlantica;* the yeast *Saccharomyces cerevisiae* and the marine diatom *Nitzschia cylindrus.*

A preferred source is the seed oil of plants known to contain significant amounts, i.e. greater than 10%, of nervonic acid in the lipid (usually triglyceride). Clearly other sources containing less than 10% can be used, but are of lower value since higher concentrations would have to be employed to provide the optimal amount, or the nervonic acid would require concentrating by the use of additional steps. The seed oils of Lunaria species e.g. *Lunaria biennis* are of particular value since they contain over 20% nervonic acid in the triglyceride lipid. A detailed typical composition of such an oil is shown in Table 2.

TABLE 2

FATTY ACID DISTRIBUTION IN *L.BIENNIS* SEED OIL*

| Fatty Acid | Name | Amount (%)** | Amount (%)*** |
|---|---|---|---|
| C16:0 | Palmitic acid | 1.2 | 1.1 |
| C16:1 | oleopalmitic acid | 0.2 | 0.1 |
| C18:0 | stearic acid | 0.2 | 0.2 |
| C18:1 | oleic acid | 23.4 | 23.3 |
| C18:2 | linoleic acid | 4.8 | 5.4 |
| C18:3 | linolenic acid | 1.0 | 0.8 |
| C20:0 | eicosanoic acid | tr**** | —***** |
| C20:1 | eicosenoic acid | 1.6 | 0.5 |
| C22:0 | behenic acid | 0.2 | 0.2 |
| C22:1 | erucic acid | 45.3 | 45.1 |
| C22:2 | docosandienoic acid | 0.1 | 0.2 |
| C24:0 | tetracosanoic acid | 0.2 | 0.1 |
| C24:1 | nervonic acid | 21.8 | 22.8 |
|  |  | 100.00 | 100.00 |

*Analysed by gas chromatography
**The triglycerides ester converted to the corresponding methyl ester
***second determination on a different sample
****trace amount, usually less than 0.1%
*****not detected In addition to the various natural sources of nervonic acid described above, it is also possible to provide nervonic acid by a synthetic procedure. The starting point for such synthesis could be, for example, the readily available erucic acid (cis-docosa-13-enoic acid). One possible synthesis has been described by Carrol K. K, Canadian J. Chem., 1957, 35, pages 757–760. This synthesis involves the conversion of erucic acid to its methyl ester by esterification with methanol, reduction to erucyl alcohol using lithium aluminium hydride, conversion of the alcohol to its alkyl bromide by reaction with phosphorous tribromide, reaction of the erucyl bromide with diethyl malonate and decarboxylation to yield nervonic acid. This synthesis is particularly advantageous in the preparation of isotopically labelled nervonic acid.

The various methods of extracting seed oils from the oil-bearing seeds are well known to those skilled in the art. These methods include dry rendering, wet rendering, batch pressing, continuous pressing, solvent extraction and extraction with super-critical gases such as carbon dioxide. In practice, the most efficient processes involve continuous pressing or super-critical extraction with or without secondary solvent extraction of the oil seed cake.

Extracted oils free from solvent may also contain undesirable impurities which can detract from the value of the oil as a pharmaceutical. Undesirable impurities or contaminants may be removed by various refining processes. Refining is defined as any purifying treatment designed to remove free fatty acids, phosphatides, gums or other major impurities.

The oil may be further improved by bleaching and deodorisation. Bleaching is defined as any process designed to reduce the colour of the oil. Various methods are used and are well known to those skilled in the art. Deodorisation is defined as any process designed to remove trace contaminants that give rise to flavour and odour. A particularly valuable purification process which has the advantage of refining, bleaching and deodorisation in one step is adsorption chromatography.

As can be seen from Table 2 above, natural oils contain a large number of component fatty acids in addition to the long chain fatty acids. If desired, the long chain fatty acids may be concentrated by selectively removing other components. Suitable methods include conversion of the triglyceride to the free fatty acid or lower alkyl ester, particularly their methyl or ethyl esters. Concentration may then be effectively performed by fractional distillation, crystallisation, solvent extraction, urea clathration or chromatography to yield nervonic acid-rich fractions. In some cases, it may be desirable to use combinations of these techniques.

Although the acids and their functionally active derivatives may be prepared synthetically by the processes described above, the processes involve a number of stages and high cost. It is especially preferred, therefore, that the materials be obtained from naturally-occurring seed oils or micro-organisms. Particularly preferred are seed oils such as those described above, and especially the seed oil of the Lunaria family.

As described above, complex triglycerides containing nervonic acid and other fatty acids can be used in the baby or infant composition, supplement for the baby or infant composition, adult foodstuff or supplement for the adult foodstuff. Such complex triglycerides can be prepared by a number of methods. These include interesterification, transesterification and related esterification techniques.

Thus, a mixture of triglycerides containing the required fatty acyl groups can be interesterified by heating, in the presence of a catalyst such as sodium hydroxide, of lipolytic enzyme until the acyl groups are randomly distributed. Alternatively, a triglyceride can be transesterified by heating in the presence of a catalyst and an alkyl ester of the fatty acids of interest.

A further possibility is complete chemical synthesis by reacting glycerol with the fatty acids required, in the presence or absence of a catalyst, with the elimination of water.

Structured (rather than mixed) triglycerides can also be prepared, where the specific fatty acids are located regiospecifically on the triglyceride. Regiospecificity can be introduced by the use of enzymes or by protecting-deprotecting methodologies. These techniques are well known to those skilled in the art and are discussed in several publications, e.g. Jensen, R. G., in "Topics in Lipid Chemistry", Vol 3, pages 1–35, ed. Gunstone, F. D. and Wiley, J. (1972) and Gunstone, F. D., in "The Lipid Handbook", 2nd edition, pages 366–374, ed. Gunstone, F. D., Harwood, J. L. and Padley, F. B. Chapman and Hall (1994).

It is further preferred that the nervonic acid or functional derivatives thereof are administered in an acceptable form. Many such forms are known and include oral administration of the oil itself, the free fatty acids or functional derivatives thereof. Additionally, the oil-free fatty acids or functional derivatives may be administered as capsules, tablets or emulsions in water. Furthermore, the composition may be administered where appropriate by injection, intravenous intubation or nasogastric intubation, for example.

Where the baby or infant composition of the invention is intended to be a formula for preterm babies or term babies and infants, many other nutrients are suitably present. Typically, the baby or infant composition would contain other fats, carbohydrates, proteins, amino acids, mineral salts, nucleosides, nucleotides and vitamins, in addition, for example, to the nervonic acid, functional derivative of nervonic acid or Lunaria oil. The infant formula may be a ready-to-feed liquid water-based preparation or may be in the form of a powder or concentrated liquid intended to be diluted with water to become a ready-to-feed liquid.

Suitable protein sources include casein, whey protein, soyabean protein, cows milk protein or hydrolysed whey or casein protein. Suitable carbohydrate sources include lactose, sucrose, glucose or glucose polymers or combinations.

In addition, the infant formula can contain nutritionally acceptable quantities of the following vitamins and minerals: vitamin A, vitamin D, vitamin B, vitamin $B_2$, Niacin, vitamin $B_6$, folate, pantothenic acid, vitamin $B_{12}$, biotin, vitamin C, vitamin E, vitamin K, calcium, phosphorous, potassium, sodium, chloride, magnesium, iron, copper, zinc, manganese, iodine and selenium.

The amino acids typically added include: L-arginine, L-cystine, L-histidine, L-isoleucine, L-leucine, L-cysteine, L-methionine, L-phenylalanine, L-threonine, L-tryptophan, L-tyrosine, L-valine, L-carnitine and taurine.

The additional fatty acids which may be incorporated as fatty acids, esters or natural oils may be saturated or unsaturated and include short chain fatty acids, long chain fatty acids, mono-unsaturated fatty acids, poly-unsaturated fatty acids, (n-6) poly-unsaturated fatty acids and (n-3) poly-unsaturated fatty acids. (n-3) and (n-6) indicate the position of the first carbon-carbon double bond with respect to the terminal methyl group on the fatty acid.

It will be understood, therefore, that the baby or infant composition of the present invention or adult foodstuff may comprise nervonic acid or functional derivatives thereof and one or more additional fatty acids. The baby or infant composition or adult foodstuff may, for example, contain a physical mixture of nervonic acid (or a derivative thereof) and the other fatty acids given above (or derivatives thereof). Alternatively, the baby or infant composition or adult foodstuff may contain structured or mixed complex triglycerides containing nervonic acid and other fatty acids, whereby all the desired fatty acids are chemically combined in the triglyceride(s).

Where the nervonic acid is supplied as Lunaria oil (which contains about 20% nervonic acid), then the amount of Lunaria oil in the baby or infant formula of the present invention would be between about 25–30 mg/100 ml feed; the minimum daily intake being about 150 mg/day or 37.6 mg/kg body weight.

By way of comparison, the normal total fat content in infant formulae is 3.4 g/100 ml (Cow and Gate Nutrition Plus), 3.41 g/100 ml (Boots Follow-On) and 3.6 g/100 ml (Milupa Aptamil). Infant formulae are often supplied as powdered concentrates to be diluted with water for feeding, in which case the concentrated powder would be formulated to provide the desired amount of nervonic acid in the final feed.

It is believed that the quantity of nervonic acid which should suitably be supplied to pregnant women, women who intend to become pregnant and lactating women is about 5–80 mg/day, preferably about 5–50 mg/day and most preferably about 8–32 mg/day. If, for example, Lunaria oil is encapsulated to give 1000 mg capsules (200 mg nervonic acid), a 50 kilogram woman would need to take between two and eight capsules per day.

Average milk volume outputs from lactating mothers range from about 600 ml/24 hours at one month, up to a maximum of about 1000 ml/24 hours at six months, and thereafter fall to around 800 ml/24 hours at twelve months. For infant formula feeding, it is recommended to give infants from about 510 ml of the feed at two weeks old to about 1000 ml at six months old.

It is proposed that the amount of nervonic acid (calculated on a 100% basis) which should suitably be taken by the infant would be in the range of about 30–60 mg/day, and that this amount could be provided by the composition of the present invention, supplied as an infant formula. The amount of nervonic acid supplied as a derivative in an infant formula in accordance with the present invention, would suitably be between about 1–20 mg/100 ml, preferably between about 2–10 mg/100 ml, and most preferably between about 4–7 mg/100 ml. As the amount of infant formula feed increases from about 600 ml (at two weeks) to about 1000 ml (at six months), the amount of nervonic acid derivative in the feed is suitably between 5–6 mg/ml. The amount of nervonic acid supplied in the infant formula needs to be sufficient to allow the infant to obtain at least the minimum daily intake of nervonic acid required, allowing for fat digestion, absorption and subsequent metabolic processing.

Where the nervonic acid is supplied as Lunaria oil (which contains about 20% nervonic acid), then the amount of Lunaria oil in the infant formula of the present invention would be between about 25–30 mg/100 ml feed; the minimum daily intake being about 150 mg/day or 37.6 mg/kg body weight.

By way of comparison, the normal total fat content in infant formulae is 3.4 g/100 ml (Cow and Gate Nutrition Plus), 3.41 g/100 ml (Boots Follow-On) and 3.6 g/100 ml (Milupa Aptamil). Infant formulae are often supplied as powdered concentrates to be diluted with water for feeding, in which case the concentrated powder would be formulated to provide the desired amount of nervonic acid in the final feed.

It is believed that the quantity of nervonic acid which should suitably be supplied to pregnant women, women who intend to become pregnant and lactating women is about 5–80 mg/day, preferably about 5–50 mg/day and most preferably about 8–32 mg/day. If, for example, Lunaria oil is encapsulated to give 1000 mg capsules (200 mg nervonic acid), a 50 kilogram woman would need to take between two and eight capsules per day.

I claim:

1. A baby or infant food composition comprising one or more nutrient materials selected from the group consisting of carbohydrates, proteins, amino acids, mineral salts, nuclocides, nucleotides and vitamins and, as a supplement, nervonic acid or a functional derivative of nervonic acid which contains the intact acyl group of nervonic acid selected from the group consisting of esters, fatty acid salts and complex triglycerides or an immediate biochemical precursor of either nervonic acid or a functional derivative of nervonic acid which contains the intact acyl group of nervonic acid selected from the group consisting of esters, fatty acid salts and complex triglycerides, in a physiologically acceptable form.

2. A composition according to claim 1, wherein the nervonic acid is present in the form of an ester thereof.

3. A composition according to claim 2, wherein the ester is a triglyceride ester.

4. A composition according to claim 1, wherein the nervonic acid or functional derivative thereof comprises at least 0.5 wt % of the composition.

5. A composition according to claim 1, which comprises erucic acid as a biochemical precursor of nervonic acid.

6. A composition according to claim 1, wherein the nutrient material also includes fats.

7. A composition according to claim 1, wherein at least part of the supplement is an oil from a plant or microorganism.

8. A composition according to claim 7, wherein the oil is the seed oil of *Lunaria biennis*.

9. A composition according to claim 1 in a form for administration to babies or infants by injection, intravenous intubation, nasogastric intubation or oral administration.

10. A food supplement comprising at least one foodstuff selected from baby, infant and adult foodstuffs and at least 0.5% nervonic acid.

11. The food supplement of claim 10, wherein the amount of nervonic acid contained in the foodstuff is 0.5–50%.

12. A pharmaceutical composition in the form of granules, powders, tablets or pills containing between 0.5 and 90% of nervonic acid and a pharmaceutically acceptable carrier.

13. A method of supplementing a baby or infant's dietary intake, said method comprising administering to a baby or infant nervonic acid or a functional derivative of nervonic acid which contains the intact acyl group of nervonic acid selected from the group consisting of esters, fatty acid salts and complex triglycerides or an immediate biochemical precursor of either said nervonic acid or said functional derivative thereof to supplement the baby or infant's dietary intake.

14. The method of supplementing an adult's dietary intake, said method comprising administering to said adult nervonic acid or a functional derivative of nervonic acid which contains the intact acyl group of nervonic acid selected from the group consisting of esters, fatty acid salts and complex triglycerides or an immediate biochemical precursor of either said nervonic acid or said functional derivative thereof.

15. The method of according to claim 14, wherein the adult is a woman who intends to become pregnant, pregnant women and lactating women.

16. The method of supplementing a baby or infant's dietary intake, said method comprising administering a composition comprising at least one nutrient material in combination with nervonic acid, a functional derivative of nervonic acid which contains the intact acyl group of nervonic acid selected from the group consisting of esters, fatty acid salts and complex triglycerides or an immediate biochemical precursor of either said nervonic acid or said functional derivative thereof to a baby or infant.

17. The method of supplementing the dietary intake of an adult having a normal level of nervonic acid in the body, said method comprising administering a composition comprising one or more nutrient materials in combination with nervonic acid, a functional derivative of nervonic acid which contains the intact acyl group of nervonic acid selected from the group consisting of esters, fatty acid salts and complex triglycerides or an immediate biochemical precursor of said nervonic acid or said functional derivative thereof to said adult.

18. The method according to claim 17, wherein the adult is a woman who intends to become pregnant, pregnant women and lactating women.

19. The method of treating pre-term and term babies and infants, women who intend to become pregnant, pregnant women, lactating women, and adults having a normal level of nervonic acid in the body by administering a composition comprising nervonic acid or a functional derivative of nervonic acid which contains the intact acyl group of nervonic acid selected from the group consisting of esters, fatty acid salts and complex triglycerides or an immediate biochemical precursor of either said nervonic acid or said functional derivative thereof in a physiologically acceptable carrier.

20. A foodstuff for a woman who intends to become pregnant, a pregnant woman or a lactating woman, which woman has a normal level of nervonic acid in the body, to which foodstuff is added nervonic acid or a functional derivative thereof or an immediate biochemical precursor of either nervonic acid or a functional derivative thereof.

21. A composition according to claim 1, wherein the nervonic acid is present in the form of a triglyceride ester thereof.

22. A composition according to claim 21, wherein the triglyceride ester contains, in addition to an acyl group of nervonic acid, one or more acyl groups of other fatty acids selected from the group consisting of (n-3)polyunsaturated fatty acids and (n-6)polyunsaturated acids.

23. A composition according to claim 21, wherein the triglyceride ester contains, in addition to an acyl group of nervonic acid, one or more acyl groups of other fatty acids selected from tie group consisting of 18:3(n-3)linolenic acid, 18:4(n-3)stearaidonic acid, 20:5(n-3)eicosapentaenoic acid, 22:6(n-3)docosahexaenoic acid, 18:2(n-6)linoleic acid, 18:3(n-6)γ-linolenic acid, 20:3(n-6)dihomo-γ-linolenic acid, and 20:4(n-6)arachidonic acid.

24. A composition according to claim 1, wherein the nervonic acid is present in the form of fatty acid salt thereof selected from the group consisting of sodium, lithium, potassium, calcium and amino acid salts.

* * * * *